Figure 1:
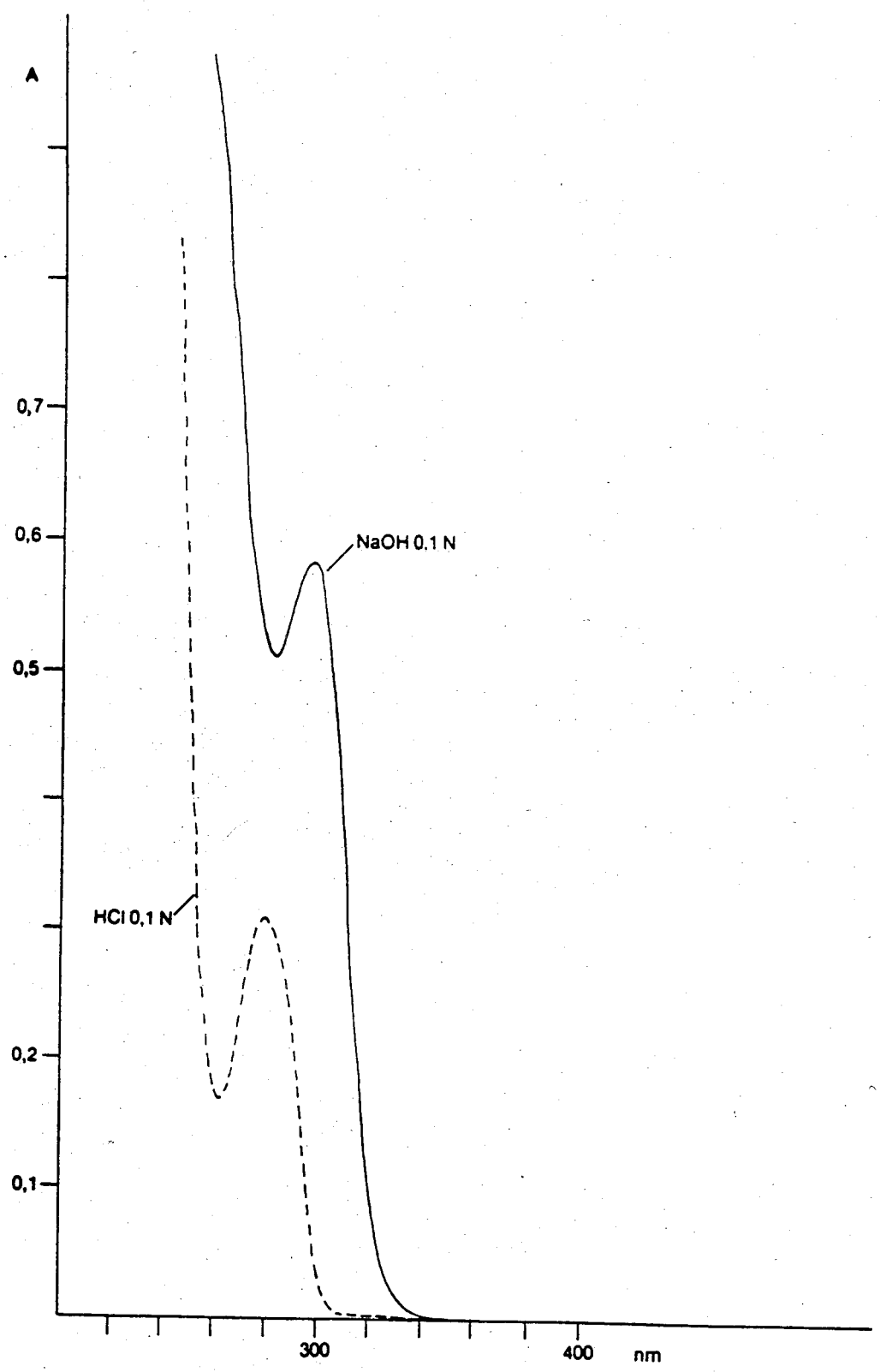

United States Patent [19]

Strazzolini et al.

[11] Patent Number: 4,629,781

[45] Date of Patent: Dec. 16, 1986

[54] CHEMICAL PROCESS FOR PREPARING L 17392 (DEGLUCOTEICOPLANIN) AND ITS SALTS

[75] Inventors: Paolo Strazzolini, Fiume Veneto; Adriano Malabarba; Bruno Cavalleri, both of Milan, all of Italy

[73] Assignee: Gruppo Lepetit S.p.A., Milan, Italy

[21] Appl. No.: 680,435

[22] Filed: Dec. 11, 1984

[30] Foreign Application Priority Data

Dec. 16, 1983 [GB] United Kingdom ............... 8333624
Jun. 13, 1984 [GB] United Kingdom ............... 8415091

[51] Int. Cl.$^4$ ................................................ C07K 5/12
[52] U.S. Cl. .................................................. 530/317
[58] Field of Search ................... 260/112.5 R; 530/317

[56] References Cited

FOREIGN PATENT DOCUMENTS 0119575 9/1984 European Pat. Off. .

OTHER PUBLICATIONS

The Journal of Antibiotics, (1978) 170–177, vol. 31.

Primary Examiner—Delbert R. Phillips
Attorney, Agent, or Firm—Stephen L. Nesbitt

[57] ABSTRACT

The present invention is directed to a chemical process for preparing antibiotic L 17392 (deglucoteicoplanin) and its salts with bases and acids by submitting a teicoplanin compound or a teicoplanin-like compound to controlled strong acidic hydrolysis conditions.

19 Claims, 3 Drawing Figures

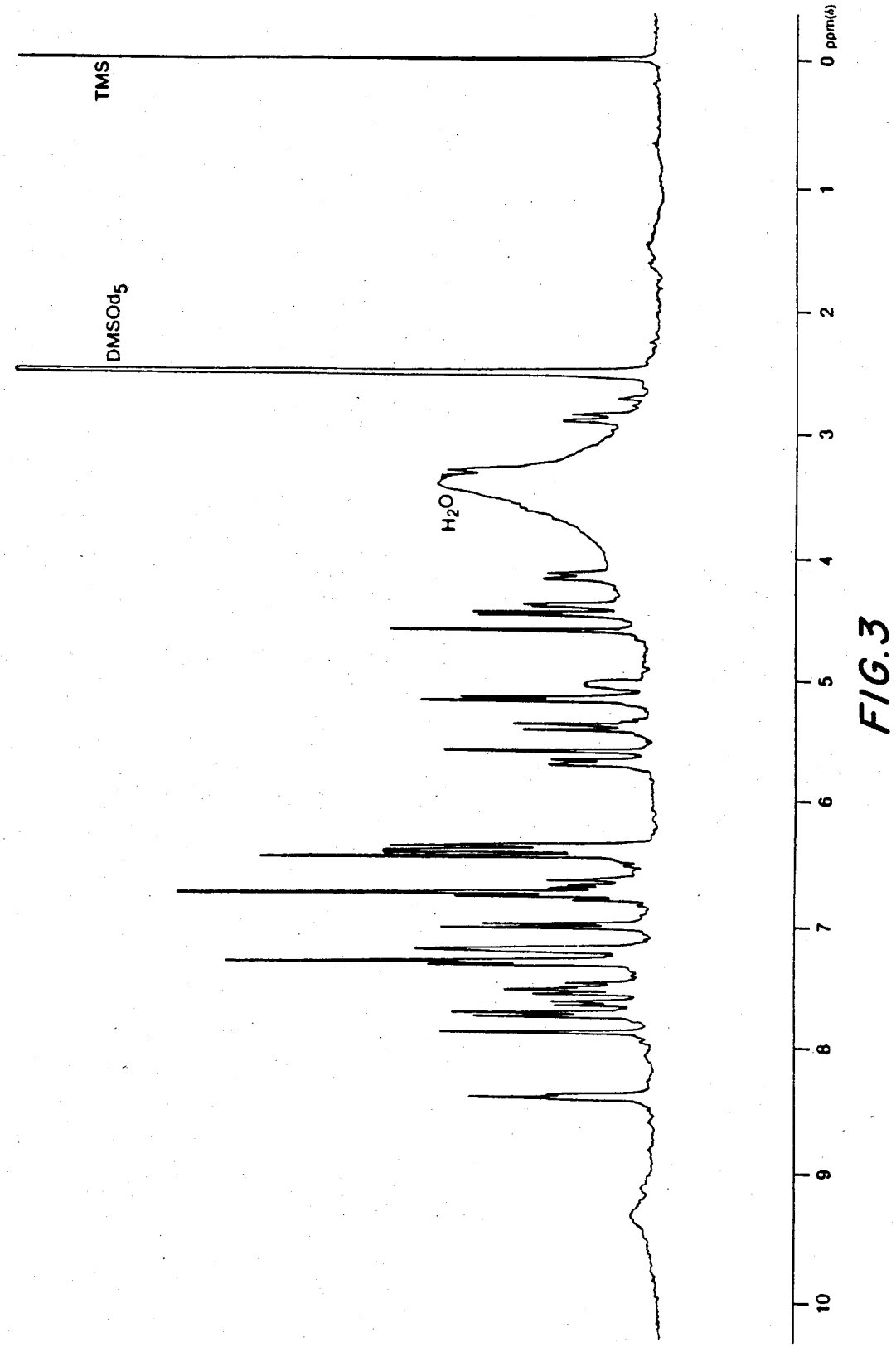

CHEMICAL PROCESS FOR PREPARING L 17392 (DEGLUCOTEICOPLANIN) AND ITS SALTS

The present invention is directed to the obtainment of an antibiotic substance arbitrarily designated as antibiotic L 17392 or deglucoteicoplanin and its salts with bases and acids.

This antibiotic substance possesses antimicrobial activity mainly against gram-positive bacteria (e.g. Staphylococcus and Streptococcus strains). This antibiotic is obtained by chemical transformation of a teicoplanin compound or teicoplanin-like compound.

Teicoplanin is the international non-proprietary name (INN) of the antibiotic substance formerly named teichomycin which is obtained by cultivating the strain *Actinoplanes teichomyceticus* nov.sp. ATCC 31121 in a culture medium containing assimilable sources of carbon, nitrogen and inorganic salts (see U.S. Pat. No. 4,239,751). According to the procedure described in the above cited patent, an antibiotic complex (identified as teichomycin) containing factors $A_1$, $A_2$ and $A_3$ is recovered from the fermentation broth by extraction with a suitable water insoluble organic solvent and precipitation from the organic solvent according to common procedures. Factor $A_2$, which is the preponderant factor of the isolated antibiotic complex, is then separated from the other factors by means of column chromatography on Sephadex®. Factor $A_1$ and factor $A_3$ are present only in minor amounts.

British Patent Application Publication No. 2121401 discloses that antibiotic factor $A_2$, in turn, actually is a mixture of five closely related co-produced main components.

From fermentation and purification (for instance, through column chromatography) operations a teicoplanin product is currently obtained which essentially consists of factor $A_2$ accompanied by minor amounts of factor $A_3$. Recent studies shows that teicoplanin factor $A_2$ and its individual main components may be represented by the following formula I

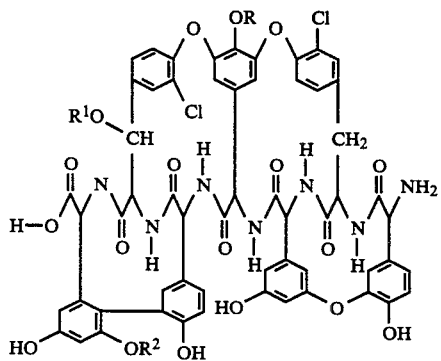

wherein
R is a N-[$C_{10}$-$C_{11}$]aliphatic acyl]-D-glucosamine rest,
$R^1$ is a N-acetyl-D-glucosamine rest, and
$R^2$ is a D-mannose rest.

All sugar moieties identified above are linked to the core molecule through O-glycosidic bonds.

A substance having the same structural formula is disclosed in European Patent Application Publication No. 0090578 and is named antibiotic A 41030 factor B. This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

In the copending European patent applications 84102665 and 84102666 have been described partial hydrolysis products of teicoplanin's factor $A_2$ wherein one or two sugar moieties are split off. These products are respectively named antibiotic L 17054 and L 17046. The products are obtained by submitting teicoplanin factor $A_2$ to some specific acid hydrolysis conditions. For L 17054 the hydrolysis is preferably carried out by using 0.5N hydrochloric acid at a temperature between 70° C. and 90° C. for 15 to 90 minutes. For L 17046, the hydrolysis is preferably carried out by using hydrochloric acid at a concentration from 1N to 3N at a temperature between 70° C. and 90° C. for 30 to 60 minutes.

Antibiotic L 17054 may be represented by the formula I above, whereby R is replaced by hydrogen, $R^1$ is a N-acetyl-D-glucosamine rest and $R^2$ is a D-mannose rest. Antibiotic L 17046 may be represented by the formula I above wherein R and $R^2$ are both replaced by hydrogen and $R^1$ is a N-acetyl-D-glucosamine rest.

In this specification and claims, with the term "teicoplanin compound" it is indicated a substance selected from the teicoplanin complex obtained by fermentation of *Actinoplanes teichomyceticus* ATCC 31121 followed by purification operations according to U.S. Pat. No. 4,239,751, any further purified preparation thereof, teicoplanin factor $A_2$, teicoplanin factor $A_3$, each of the main components of teicoplanin factor $A_2$. With the term "teicoplanin-like compound" it is hereby indicated any compound having the same basic structure formula I as above wherein R is hydrogen, $R^1$ is hydrogen or a N-acetyl-D-glucosamine rest, $R^2$ is hydrogen or a D-mannose rest with the proviso that R, $R^1$ and $R^2$ cannot be simultaneously hydrogen, and a mixture of two or more of any of the above substances and/or compounds in any proportion.

According to the object of this invention it has been found that antibiotic L 17392 (deglucoteicoplanin) and its salts with bases and acids may be obtained by submitting to controlled strong acidic hydrolysis conditions a teicoplanin compound or a teicoplanin-like compound.

The "controlled strong acidic hydrolysis conditions" which are suitable for the process of this invention are those reaction conditions whereby it is provided sufficient acid strength to provoke the removal of all sugar moieties of teicoplanin compounds and/or teicoplanin-like compounds without simultaneously provoking other undesired modifications or alteration of the chemical structure and chiral centers of the substrate.

It is known that removal of all sugars moieties from a complex molecular structure such as that of glycopeptide antibiotics always present considerable difficulties since mild acid hydrolysis conditions usually afford only partial removal of sugars moieties while strong acid hydrolysis conditions promote partial degradation of the substrate and/or changes in the stereochemical configuration of chiral centers. For instance, for avoparcin, a known glycopeptide antibiotic, the true aglycone was never isolated.

The following scientific literature support the above considerations: G. A. Ellestad et al., J. of Antibiotics, 36, 1683 (1983); C. M. Harris et al., J. Am. Chem. Soc. 105, 6915 (1983); W. J. McGahren et al., J. of Antibiotics, 36, 1671 (1983). M. R. Bardone et al. (J. of Antibiotics, 31, 170 (1975)) describes hydrolytic treatments of teichomycin factor $A_2$ both with aqueous 2N $H_2SO_4$ and with aqueous 6N HCl at 100° C. In no case the true aglycone of teicoplanin is obtained. There is no indication whatever in the above cited literature which suggest to employ any specific hydrolysis condition to transform a teicoplanin compound or teicoplanin-like compound into the corresponding teicoplanin aglycone (or deglucoteicoplanin).

According to the object of this invention the "controlled strong acidic hydrolysis conditions" outlined above are provided by properly selecting the solvent, the type of acid, its concentration, and the temperature of the reaction. In fact, it is hereby provided a process for transforming a teicoplanin compound or a teicoplanin-like compound into deglucoteicoplanin and its salts with bases and acids, characterized in that a substance selected from teicoplanin complex, any further purified preparation thereof, teicoplanin factor $A_2$, teicoplanin factor $A_3$, each of the main components of teicoplanin factor $A_2$, a compound of formula I above wherein R is hydrogen, $R^1$ is hydrogen or a N-acetyl-D-glucosamine rest, $R^2$ is hydrogen or a D-mannose rest with the proviso that R, $R^1$ and $R^2$ cannot be simultaneously hydrogen, and a mixture of two or more of any of the above substances in any proportion, is submitted to controlled strong acid hydrolysis. The process of this invention is further characterized in that the controlled strong acid hydrolysis conditions are provided by employing (a) an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry ($C_1$-$C_4$) alkyl, ($C_1$-$C_4$)alkoxy or halo rests which at the reaction temperature are liquids slightly mixable with water, and beta-polyhalogenated lower alkanols, which at the reaction temperature are liquids, (b) a strong acid compatible with the solvent selected from strong mineral acids, strong organic acids and strong acid cation exchanger resins in the hydrogen form, and (c) a reaction temperature between about 20° C. and about 100° C. When the protic solvent is selected from aliphatic acids and alpha-halogenated aliphatic acids, aliphatic acids of 1 to 5 carbon atoms, and alpha-halogenated aliphatic acids of 2 to 5 carbon atoms are respectively preferred, although any aliphatic acid and any alpha-halogenated aliphatic acid which, at the reaction temperature, is capable of dissolving a teicoplanin compound or teicoplanin-like compound in sufficient amount, may be usefully employed.

The term "in sufficient amount" is hereby intended to mean that the concentration of the compound in the solvent under the reaction condition is not so low that the reaction rate is very slow and/or a huge amount of solvent is required to perform the reaction in a pilot or industrial scale.

Since the teicoplanin compounds and the teicoplanin-like compounds contain functional groups, such as hydroxy and amino, which might react with aliphatic acids and alpha-halogenated aliphatic acids, a further condition for the successful employment of the above mentioned acids as the solvents for carrying out the controlled strong acid hydrolysis is that said acids do not react with the substrate yielding undesired functional derivatives of the same teicoplanin and teicoplanin-like compounds. Examples of the above acids are: formic acid, acetic acid, propionic acid, butyric acid, isobutyric acid, valeric acid, isovaleric acid, trimethylacetic acid, fluoroacetic acid, chloroacetic acid, difluoroacetic acid, dichloroacetic acid, trifluoroacetic acid, trichloroacetic acid, pentafluoropropionic acid, 2,2,3,4,4,4-hexafluorobutyric acid, heptafluorobutyric acid and the like.

When said above mentioned aliphatic acids and alpha-halogenated aliphatic acids are used as the solvents for the controlled strong acid hydrolysis reaction, it is preferred to carry out the reaction in the presence of a certain amount of water. In general, the amount of water ranges between 2.5% and 25% by weight on the total solvent although a lower amount may be employed, in particular, with those acids which are very slightly mixable with water. The desired amount of water can be originally dissolved in the acid solvent or, when addition of a strong acid as the hydrolysis promoter is necessary, it can be added together with said strong acid. According to a preferred way to carry out this reaction, a predetermined amount of a concentrated aqueous mineral acid, such as hydrochloric acid, hydrobromic acid and sulfuric acid, is added to a mixture of teicoplanin or teicoplanin-like compound in a lower aliphatic acid (e.g. acetic acid) and the mixture is then heated at a temperature between 40° C. and 100° C., preferably between 65° C. and 85° C., for a time necessary to achieve a satisfactory yield of deglucoteicoplanin as determined through. analytical tests.

Lower aliphatic acids such as acetic acid and propionic acid or lower alpha-halogenated aliphatic acid such as chloroacetic acid, dichloroacetic acid, trichloroacetic acid, difluoroacetic acid, chlorodifluoroacetic acid, trifluoroacetic acid and pentafluoropropionic acid are preferred reaction solvents according to one embodiment of this invention. Among these acid solvents, those possessing high acid strength may simultaneously act both as solvents and as strong acid promoting the hydrolysis reaction and thus there is no need of a further addition of a strong acid to promote the hydrolysis reaction. For this purpose, trifluoroacetic acid proved to be particularly useful when employed at a concentration between 75% and 95% at a temperature between 60° and 90° C. for a reaction time varying from 0.5 hour to 8 hours. When the protic solvent is selected from aliphatic alkanols and cycloaliphatic alkanols which at the reaction temperature are liquids slightly mixable with water, primary and secondary alkanols of at least five carbon atoms and secondary cycloalkanols of at least five carbon atoms are usually preferred. Because of a more suitable handling during the procedure of recovering the reaction product, alkanols which are liquids at the room temperature are the most preferred ones. The above said primary and secondary alkanols may have straight or branched hydrocarbon chains. Said chains may also bear acid inert unsaturations and/or include cycloaliphatic rests. Commercially available alkanols with the above characteristics have in general a number of carbon atoms between 5 and 12, although any primary or secondary aliphatic and secondary cycloaliphatic alkanol having the above illustrated properties may be employed according to the process of this invention.

According to a most preferred embodiment of this invention, primary and secondary alkanols and secondary cycloalkanols of 5 to 10 carbon atoms are usefully employed as the reaction solvent of the controlled strong acid hydrolysis of this invention. Examples of said alkanols are:

1-pentanol, 2-pentanol, 3-pentanol, 1-hexanol2-hexanol, 3-hexanol, 3,3-dimethyl-1-butanol, 4-methyl-1-pentanol;
3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol.

For the use as solvents in the controlled strong acid hydrolysis the above alkanols are usually employed in the presence of a water phase and a strong acid as the hydrolysis reaction promoter. According to a typical example of the use of the above alkanols in the controlled strong acid hydrolysis, a teicoplanin compound or teicoplanin-like compound is contacted with a concentrated mineral acid such as aqueous hydrochloric acid (20% to 37% w/v), aqueous hydrobromic acid (20% to 62%, w/v) and aqueous sulfuric acid (10% to 60% w/v), in the presence of a large molecular excess of 1-octanol at a temperature between 35° C. and 100° C., preferably between 40° C. and 80° C., for from about 4 hours to about 40 hours giving deglucoteicoplanin with good yield.

When the organic protic solvent is selected from phenyl substituted lower alkanols wherein the phenyl moiety may optionally carry ($C_1$-$C_4$)alkyl, ($C_1$-$C_4$)alkoxy or halo rests, which at the reaction temperature are slightly mixable with water, the lower alkanol portion preferably is a primary or secondary alcohol portion of 1 to 4 carbon atoms, although any phenyl substituted alkanol which at the reaction temperature is capable of dissolving a teicoplanin compound or teicoplanin-like compound in sufficient amount, may be suitably employed. Also in this case, a desirable characteristic of the solvent is that of allowing easy handling of the reaction mixture during the process of recovering the reaction product and, therefore, those above mentioned phenyl-substituted lower alkanols which are liquids at the room temperature are the most preferred ones. Examples of said phenyl substituted lower alkanols are the following:

benzyl alcohol, m-chlorobenzyl alcohol, o-fluorobenzyl alcohol, m-fluorobenzyl alcohol, p-fluorobenzyl alcohol, m-methylbenzyl alcohol, m-methoxybenzyl alcohol, o-ethoxybenzyl alcohol, m-butoxybenzyl alcohol, p-tert.butoxybenzyl alcohol, p-tert.butylbenzyl alcohol, phenethyl alcohol, o-chlorophenethyl alcohol, m-chlorophenethyl alcohol, o-methoxyphenethyl alcohol, m-methoxyphenethyl alcohol, o-propylphenethyl alcohol, o-ethoxyphenethyl alcohol, p-fluorophenethyl alcohol, p-bromophenethyl alcohol, o-propoxyphenethyl alcohol, o-butoxyphenethyl alcohol, 1-(p-isopropylphenyl)ethanol, 3-phenyl-1-propanol, 2-phenyl-1-propanol, 4-phenyl-1-butanol and 3-phenyl-1-butanol.

For the use as solvents in the controlled strong acid hydrolysis the above phenyl-substituted lower alkanols are usually employed in the presence of a water phase and a strong acid as the hydrolysis reaction promoter. According to a typical example of the use of the above phenyl substituted lower alkanols in the controlled strong acid hydrolysis, a teicoplanin compound or teicoplanin-like compound is contacted with a concentrated mineral acid such as aqueous hydrochloric acid (20% to 37%, w/v), aqueous hydrobromic acid (20% to 62%, w/v) and aqueous sulfuric acid (10% to 60% w/v), in the presence of a large molecular excess of benzyl alcohol at a temperature between 35° C. and 100° C., preferably between 40° C. and 80° C., for from about 4 hours to about 40 hours giving deglucoteicoplanin with good yields.

When the organic protic solvent is selected from beta-polyhalogenated lower alkanols which at the reaction temperature are liquids, beta-chloro- and/or fluoro-substituted alkanols of 1 to 4 carbon atoms are preferred. Examples of said beta-polyhalogenated lower alkanols are:

dichloroethanol, trichloroethanol, dichlorofluoroethanol, difluorochloroethanol, difluoroethanol, trifluoroethanol, 1,1,1,3,3,3-hexafluoro-2-propanol, 2,2,3,4,4,4-hexafluorobutanol, and 2,2,3,3,4,4,4-heptafluorobutanol.

When said above mentioned beta-polyhalogenated lower alkanols are used as the solvents for the controlled strong acid hydrolysis reaction, a certain amount of water is usually present under the typical reaction conditions. Although, from one side it may be desirable to keep the amount of water as lower as possible in order to prevent undesired side reactions such as rearrangement and/or isomerization of chiral centers of the substrate, for the purpose of increasing the reaction speed and improving the operability, the process is usually carried out in the presence of an amount of water between about 0.03 percent and about 3 percent (weight/volume) of the whole beta-polyhalogenated alkanol employed as the organic protic solvent. The water may be added to the solvent or may be originally incorporated into the teicoplanin compound or teicoplanin-like compound employed as a wet starting material. Also, a desired amount of water may be supplied together with the strong acid which is added as the hydrolysis reaction promoter to the mixture of the solvent and the starting material.

According to a typical example embodying this invention, deglucoteicoplanin is obtained in good yield by suspending a teicoplanin or teicoplanin-like compound containing about 10% of water (by weight) in a large molecular excess of trifluoroethanol in the presence of a hydrogen halide such as hydrogen chloride or hydrogen bromide, at a temperature between 35° C. and the boiling temperature of the mixture, preferably between 40° C. and 80° C., for a period of 8 to 15 hours.

According to the scope of this invention, the protic organic solvent may also consist of a mixture of two or more of the above mentioned solvents. The mixture of solvents may consist not only of two or more solvents selected from the same class such as, the aliphatic acids, the alkanols, the beta-polyhalogenated alkanols described above, etc., but it may include solvents of different type which are compatible each other. For instance, it may consist of an aliphatic or cycloaliphatic alkanol and a beta-polyhalogenated alkanol and/or a phenyl substituted lower alkanol.

Although in the description and claims the term "solvent" is widely used, according to the process of this invention it is not necessary that either the starting teicoplanin compound and/or teicoplanin-like compound or the final deglucoteicoplanin product is completely dissolved into the reaction solvent(s) to form a homogeneous reaction solution. In fact, in some cases it has been found that the controlled strong acid hydrolysis process is very effective when carried out as an heterogeneous phase reaction where both the starting material and the reaction product are only partially dissolved in the selected organic protic solvent. In some cases, the reaction mixture may actually consist of three separated phases, namely, the aprotic organic solvent phase, the strong aqueous acid phase and the solid starting material and/or final product phase. The formation of a single homogeneous phase or more heterogeneous phases at the reaction temperature mainly depends on the aprotic organic solvent, the type of the acid employed and its concentration.

In general, with solvents such as the lower aliphatic acids and the lower alpha-halogenated aliphatic acids, a homogeneous phase is obtained after heating the reaction mixture at the reaction temperature since the starting teicoplanin materials are quite soluble in this type of solvents and the strong acid added as hydrolysis reaction promoter—when needed—is also quite soluble in said solvents, either in the form of the pure acid or as an highly concentrated aqueous solution thereof. Concentrated hydrochloric or hydrobromic acid in acetic acid (as the solvent) is a typical example of a reaction system whereby the controlled strong acid hydrolysis is carried out as a homogeneous phase reaction. With the aliphatic and cycloaliphatic alkanols, and the phenyl-substituted lower alkanols defined above, the controlled strong acid hydrolysis process of this invention is preferably carried out as an heterogeneous phases reaction, in that, the reaction mixture usually consists of an organic phase (the solvent), an aqueous phase (the strong acid) and a solid phase (the starting material and the end product).

In a few cases, however, the aqueous phase may not be present since the acid is totally dissolved into the organic phase. Also, in some instances, the aqueous phase and/or the solid phase may disappear during the course of the reaction. In particular, the water phase may disappear when the reaction conditions promote evaporation, thus sensibly reducing its proportion in the reaction mixture, and/or increasing the concentration of the acid, which is then completely resorbed into the organic layer.

The solid phase may disappear during the course of reaction because of modifications occurring in the composition of the solid mixture of reactants and end products which may enhance its solubility in the organic layer.

The strong acid which is needed to provide the controlled strong acid hydrolysis conditions of the process of this invention is selected from strong mineral and organic acids as well as from strong acid cation exchanger resins (hydrogen form).

With the mineral acids, hydrohalic acids such as hydrochloric and hydrobromic acid are preferred, although other strong mineral acids such as sulfuric acid may be employed. These acids are usually employed in a high concentration and in large molar excess whether an aqueous acid solution is added to the organic solvent or a direct solution of the acid in the organic layer is prepared.

Indeed, in some cases, the hydrogen bromide and the hydrogen chloride may be dissolved into the organic protic solvent and the reaction mixture may be maintained under acid saturation conditions by bubbling the acid gas into the mixture during all the reaction time. Alternatively, a concentrated aqueous solution of the acid is added to the mixture of the organic protic solvent and the teicoplanin or teicoplanin-like compound. The concentration of the acid aqueous solution is usually ranging between 20% and 37% (w/v) for hydrochloric acid and between 20% and 62% (w/v) for the hydrobromic acid. When other aqueous mineral acids are employed, such as sulfuric acid, the concentration of the aqueous solution added to the mixture is generally over 10% (w/v), preferably between 15% and 60%. In this latter case, however, during the course of the reaction the concentration of the acid may still increase because of evaporation of water under the operational reaction conditions.

When strong organic acids are employed, they may be dissolved into the organic protic solvent or may be added to the reaction mixture as a concentrated aqueous solution thereof. Typical examples of strong organic acids which are suitably employed in the controlled strong acid hydrolysis process are the alpha-polyhalogenated lower aliphatic acid such as trichloroacetic acid, and trifluoroacetic acid. Other examples of strong organic acids which are suitable for this process are the alkanesulfonic acids, the cycloalkanesulfonic acids and the arylsulfonic acids. Specific examples of said sulfonic acids are the following:

methanesulfonic acid, trifluoromethanesulfonic acid, ethanesulfonic acid, benzenesulfonic acid, p-toluenesulfonic acid, cyclohexanesulfonic acid, camphorsulfonic acid, alpha- and beta-naphthalenesulfonic acid.

Suitable strongly acidic conditions for the process of this invention may be provided also by employing strong acid cation exchanger resins in the hydrogen form. Typically, sulfonated styrene and styrene-divinyl benzene matrix resins are employed. For example, strong acid cation exchanger resins of said type are listed in the Merck Index, Seventh Edition, pages 1579-1585. The strong acid cation exchanger resins which are commercially available, usually contain retention water. However, according to a preferred embodiment of this invention, the water content may be controlled by preparing the resin in a dry form by thoroughly washing it with methanol and successively adding the desired amount of water. In said case, the amount of water added is usually commensurate with the amount of solvents employed in order to reach the appropriate water percent content in the whole reaction mixture, according to the indications given above.

With the use of strong acid exchanger resins, a large excess (by weight) of the same resin over the teicoplanin compound or teicoplanin-like compound is usually employed and the organic protic solvent for the hydrolysis reaction is preferably selected from those solvents wherein the starting material and the final product are fairly soluble in order to obtain a complete solution and, thus, facilitating the recovery of the end product and, in particular, the separation of the resin from the reaction mixture. The organic acids such as formic acid, acetic acid and propionic acid are suitable solvents for said purpose.

Both the highly concentrated acids and the strong acid cation exchanger resins in the hydrogen form, must be compatible with the reaction solvent, in that, under the reaction conditions of the process of this invention, they must not provoke undesired side-reactions with the solvent itself.

As a general illustration of the controlled strong acid hydrolysis process, the teicoplanin compound or teicoplanin-like compound is dissolved or suspended into a large molar excess of the selected organic protic solvent which may already contain an excess of the selected strong acid. Alternatively, the strong acid may be successively added to the solution or suspension of the starting material in the organic protic solvent. This latter procedure is usually preferred with the strong acid cation exchanger resins in the hydrogen form. The reaction mixture is then maintained with stirring at the desired temperature for a period of time enough to achieve satisfactory yields of deglucoteicoplanin. The reaction time is usually determined by monitoring the reaction through analytical tests. For the purpose of giving a general indication without limiting the scope of this invention, the reaction time may generally range between 0.5 and 50 hours, depending on the starting material, the solvent(s), the strong acid, its concentration and the temperature of the reaction. The temperature of the reaction is properly selected for each reaction system, taking into accounts the following factors: the starting materials, the type of the organic protic solvent, the type and the concentration of the acid, and their mutual proportions. Lower reaction temperature usually requires a longer reaction time for obtaining satisfactory conversion yields. In general the controlled strong acid hydrolysis process is carried out at a temperature between about 20° C. and about 100° C. and, when the boiling temperature of the reaction mixture is lower than about 100° C., between about 20° C. and the boiling temperature of the mixture.

A preferred temperature range is between 35° C. and 100° C. with the range between 40° C. and 80° C. being the most preferred one.

If the hydrolysis reaction is carried out in heterogeneous liquid phase with a solvent slightly mixable with the concentrated aqueous solution of the strong acid (e.g. primary and secondary alkanols and cycloalkanols of 5 to 10 carbon atoms, phenyl substituted lower alkanols, etc.) good results are obtained by operating under reduced pressure. A reduced pressure of the order of 10 to 50 mmHg is generally preferred as the typical operational pressure.

When the strong acid employed is a gas dissolved into the reaction solvent, such as hydrogen chloride or hydrogen bromide in beta-polyhalogenated lower alkanols, and heating the mixture at the selected reaction temperature may provoke desorption of said acid and decrease of its concentration in the solvent, the acid concentration is restored by continuously bubbling the acid gas into the same reaction mixture. When the hydrolysis reaction is carried out in heterogeneous liquid phases with a solvent slightly mixable with the concentrated aqueous solution of the strong acid and the aqueous acid portion may be substantially reduced and/or the acid concentration lowered by evaporation on heating at the selected reaction temperature and pressure, the acid concentration may be restored by further additions of aqueous concentrated acid or by bubbling acid gas into the same reaction mixture. Additions of acid may be coupled with additions of solvent, particularly when operating under reduced pressure which give rise to removal of substantial amounts of solvent during the reaction time. The reaction course is usually followed through analytical tests, e.g. High Performance Liquid Chromatography (HPLC), to determine the most suitable reaction time for each specific case.

When the reaction is stopped, the recovery of the reaction product is carried out in the usual way. If two liquid phases are still present at the end of the reactions, the aqueous phase may be stripped off by evaporation under reduced pressure and then the organic layer is cooled at room temperature. If a substantial amount of end product is present as a solid precipitate, it is separated by filtration or centrifugation. The remaining organic solvent is discarded or, if HPLC tests show that it contains additional amounts of the end product, it is set apart for the recovery of said product.

When most of the end product is dissolved in the organic protic solvent, the reaction mixture is further concentrated to obtain a solid precipitate which is then separated in the usual way. Alternatively, the end product may be precipitated from the organic solution by addition of an organic solvent wherein it is substantially unsoluble such as, for instance, ethyl ether. If the strong acid which is employed is a strong cation exchanger resin in the hydrogen form, the resin is filtered off while the solution is still at the reaction temperature and then the liquid phase is worked up according to conventional procedures like those mentioned above.

Deglucoteicoplanin thus obtained is in general in the form of an acid addition salt with the same strong acid employed to provide the strong acid hydrolysis conditions of the process of this invention. Said acid addition salts can be further purified according to usual purification techniques and, in particular, by column chromatography. The acid addition salt of deglucoteicoplanin can be transformed into the acid free compound by conventional methods i.e. by applying treatment with acid acceptors such as aqueous bases solutions, aqueous solutions of ammonium salts of organic acids, basic anion exchanger resins, ethylene epoxyde, etc. If desired, the purification procedure may be combined with the acid acceptor treatment to obtain substantially pure deglucoteicoplanin. For instance, column chromatography purification may be coupled with contacting with an aqueous base solution or preferably with an aqueous solution of an ammonium salt of an organic acid.

Accordingly, a preferred purification procedure involves the use of a reverse phase column chromatography. A preferred adsorbent in this case is the silanized silica gel having a distribution particle range of 0.06–0.2 mm. The eluent can be one of the hydrophilic mixtures that can be used in this purification technique. Representative examples of these hydrophilic eluents are the mixtures of diluted aqueous solution of ammonium salts of organic acids, acetonitrile or water soluble lower alkanols. Representative examples of diluted aqueous solutions of ammonium salts of organic acids are a 0.1–6% ammonium formate aqueous solutions, while examples of suitable alkanols are methanol, ethanol, propanol and the like.

Preferred eluents are the mixtures of aqueous ammonium formate and acetonitrile at a pH between 6.5 and 7.5 or the mixtures of aqueous ammonium formate and methanol. Particularly preferred for the purification of a crude deglucoteicoplanin salt is a procedure which includes:

(a) contacting a solution of the crude deglucoteicoplanin acid addition salt in a mixture of 0.2% aqueous ammonium formate/methanol/butanol, 1:2:3, or acetonitrile/5% aqueous ammonium formate 1:9 with silanized silica gel and stripping off the solvents, (b) applying the residue at the top of a silanized silica gel (0.06–0.2 mm) column, developing with 0.6% aqueous ammonium formate and acetonitrile 9:1, discarding the eluate and continuing the elution with a linear gradient of acetonitrile in water, from 1:9 to 3:7 at a rate of 200 ml/hour for 30 hours.

The thus obtained product is substantially pure deglucoteicoplanin showing satisfactory physico-chemical and biological characteristics for use in the applications described below.

Substantially pure deglucoteicoplanin has an HPLC titre greater than 95% (percent peak areas, at the 254 nm U.V. wavelenght), a water and solvent content from 10% to 15% by weight and an inorganic residue lower than 0.5% by weight.

Crystalline pure (needles) deglucoteicoplanin may be obtained by suspending the above preparation of substantially pure deglucoteicoplanin in water/acetonitrile 9:1 and then adjusting the pH to 1.7 by adding 1N HCl. The resulting solution is then applied to a silanized silica gel column stabilized with diluted (1%) aqueous ammonium formate and the column is washed first with water and then developed with a linear gradient of acetonitrile in water from 10% to 40% at a rate of 70 ml/hours for 30 hours. The fraction collected are monitored by HPLC. The fractions containing the pure deglucoteicoplanin are pooled together and allowed to stand for 24 hours thus yielding crystalline pure deglucoteicoplanin. This procedure can be applied directly to crude teicoplanin or its acid addition salts in those cases where they are recovered from the hydrolysis reaction with sufficient purity degree. Deglucoteicoplanin as obtained according to the above procedures, has the following characteristics:

(a) it is soluble in water at a pH higher than 9 and aqueous methanol, ethanol and acetone; slightly soluble in ethyl alcohol and dimethylformamide (b) an ultraviolet absorption maxima, which is reported in FIG. 1 of the accompanying drawings, which shows the following absorption maxima:
 in 0.1N hydrochloric acid: $\lambda_{max}$ 279 nm ($E_1$ $_{cm}$1%=87.1)
 in 0.1N sodium hydroxide: $\lambda_{max}$ 297 nm ($E_1$ $_{cm}$1%=165.3)

Figure 2:
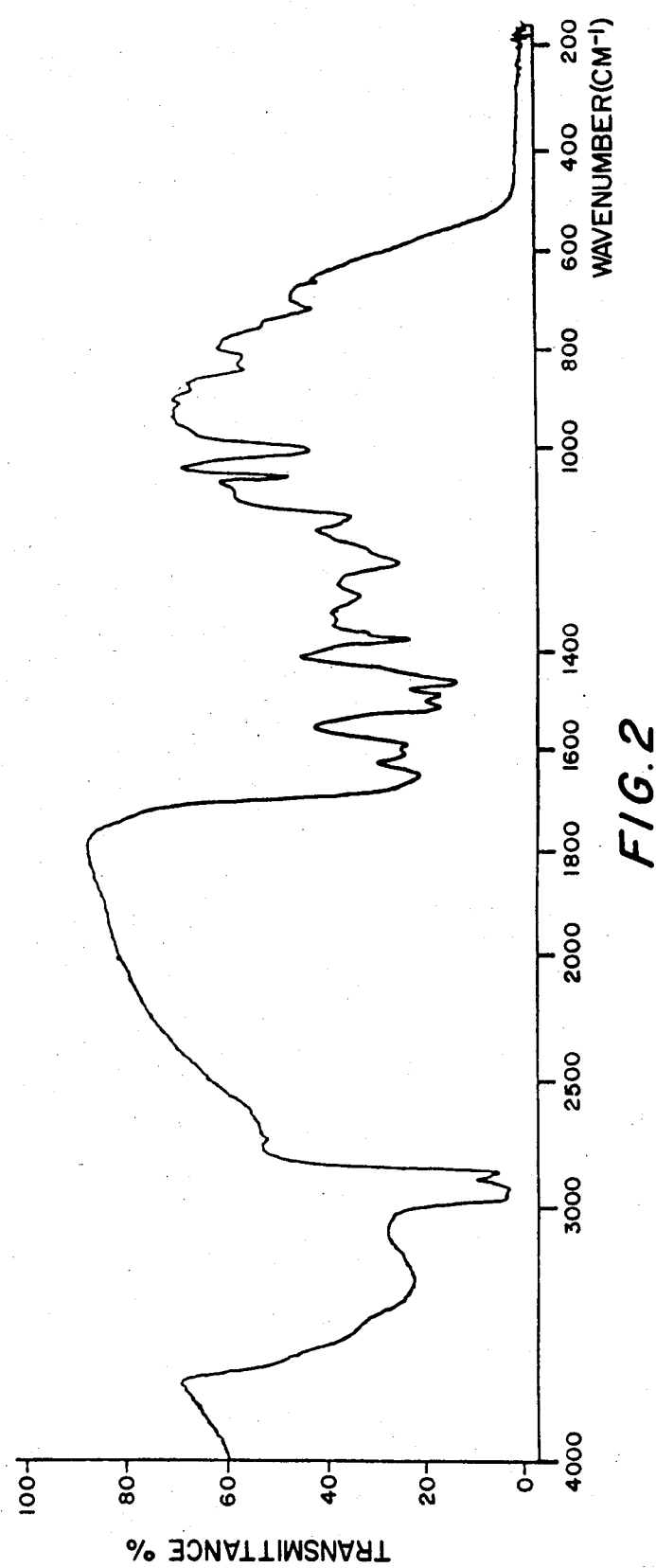

(c) an infrared absorption spectrum in nujol, shown in FIG. 2 of the accompanying drawings, with the following mainly significant absorption maxima (cm$^{-1}$):
 3250 ($\nu$NH and phenolic $\nu$OH)
 1645 (Amide I)
 1610 ($\nu$COO$^-$)
 1595 ($\delta$NH$_3^+$)
 1520 (Amide II)

(d) an $^1$H NMR spectrum registered at 270 MHz with a Bruker WH-270 Spectrometer, in DMSO-d$_6$ at 50° C. (internal standard TMS, $\delta$=0.00 ppm) as in FIG. 3. Some of the $^1$H NMR data obtained after D$_2$O exchange and selective decoupling experiments are as follows
 $\delta$(ppm), multiplicity: 2.85–3.30, 2 dd; 4.12, dd; 4.37, d; 4.45, d; 4.50, s; 5.00, ddd; 5.11, d; 5.14, d; 5.35, d; 5.56, d; 5.60, d; 6.3–7.9, m; 6.55, d; 7.37, d; 7.50, d; 7.61, d; 8.26, d; 8.28, d; 8.5–10.2, br.
 d=doublet
 dd=doublets of doublets
 ddd=doublet of doublets of doublets
 s=singlet
 m=multiplet
 br=broad (e) an elemental analysis which indicates the following approximate percentage composition (average): carbon 58.05%; hydrogen 3.58%; nitrogen 8.23%; chlorine 5.85%; (after correction for a weight loss of 11% measured by thermal gravimetric analysis).

(f) a molecular weight of 1199 confirmed also by Fast Atomic Bombardment/Mass spectrometry analysis (FAB-MS).

(g) formula [calculated on the basis of the available data]: $C_{58}H_{45}Cl_2N_7O_{18}$.

(h) a retention time ($t_R$) of 12.2 min. when analyzed by HPLC using a pre-column (5 cm) packed with Perisorb RP8 (30 $\mu$m; Merck) followed by a column Hibar RT250-4 (Merck) prepacked with LiChrosorb RP8 (10 $\mu$m) and eluting with a linear-step gradient ranging from 10% to 30% of acetonitrile in 0.2% aqueous ammonium formate; flow rate: 2 ml/min (as a reference, teicoplanin factor A$_2$, component 2 of British Patent Application Publication No. 2121401 has a $t_R$ of 22.4 min in this system)

(i) an acidic function capable of forming salts.

(l) a basic function capable of forming salts (m) no sugar residue.

On the basis of the physico-chemical data and by comparison with other glycopeptidic antibiotic substances, such as vancomycin and ristocetin, the following structure can tentatively be attributed to deglucoteicoplanin:

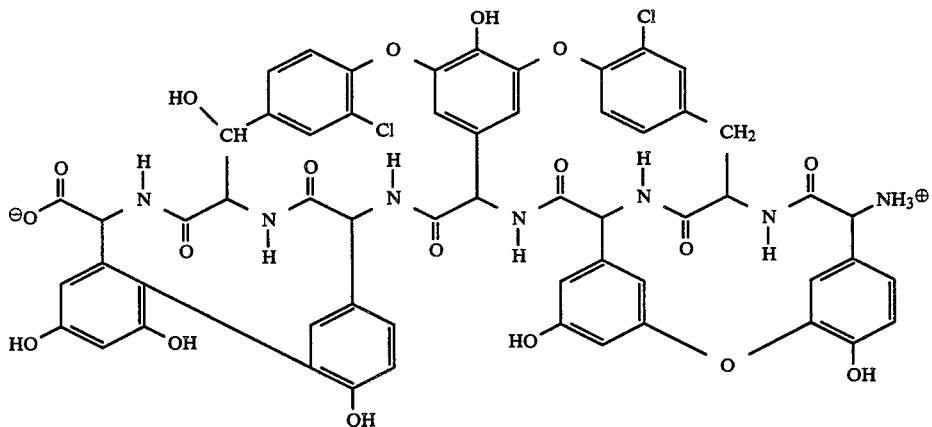

Deglucoteicoplanin possesses acid and basic functions and therefore it can be transformed into its salts with bases and acids according to procedures known per se in the art. Said methods include reacting the acid or basic function of deglucoteicoplanin with an equivalent amount of the appropriate base or acid in water (preferred procedure for the salts with bases) or in a mixture of water and butanol 30:70 (preferred procedure for the salts with acids) and lyophilizing the obtained aqueous solution (salts with bases) or concentrating the water/butanol suspension (salts with acids) to substantially eliminate the water and then adding an excess of ethyl ether (to precipitate the acid salts). The salts with acids include those with pharmaceutically acceptable acids e.g., those derived from the following acids: hydrochloric, hydrobromic, sulfuric, phosphoric, glycolic, lactic, pyruvic, malonic, succinic, fumaric, malic, tartaric, citric, ascorbic, maleic, hydroxymaleic, benzoic, hydroxybenzoic, phenylacetic, cinnamic, 2-phenoxybenzoic, methanesulfonic and 2-hydroxyethane sulfonic acid.

Among the salts with bases, the alkali metal salts and the ammonium and alkylammonium salts are preferred in view of their easy preparation and desirable solubility properties. The salts with bases also encompass salts with basic amino acids such as lysine and arginine. In view of the similarity of the properties of deglucoteicoplanin and its salts, the present application also encompasses the salts of said antibiotic substances and the process for obtaining them.

The in vitro antibacterial activity of deglucoteicoplanin was determined using the two-fold dilution method in microtiter system. Todd-Hewitt broth (Difco) was used for streptococci and Isosensitest broth (Oxoid) for staphylococci and gram-negative bacteria. Overnight broth cultures were diluted so that the final inoculum was about $10^4$ colony-forming units per ml (cfu/ml). Minimal inhibitory concentration (MIC) was read as the lowest concentration which showed no visible growth after 18–24 hours incubation at 37° C. The obtained results are reported in Table I below:

TABLE I

In vitro antibacterial activity of deglucoteicoplanin

| Organism | MIC ($\mu$g/ml) deglucoteicoplanin |
|---|---|
| Staphylococcus aureus ATCC 6538 | 0.025 |
| Staplylococcus aureus Tour | 0.05 |
| Staphylococcus aureus Tour[a] | 0.2 |
| Staphylococcus aureus Tour[b] | 0.2 |
| Staphylococcus epidermidis ATCC 12228 | 0.0125 |
| Streptococcus pyogenes C 203 SFK 13400 | 0.05 |
| Streptococcus pneumoniae UC 41 | 0.05 |
| Streptococcus faecalis ATCC 7080 | 0.1 |
| Escherichia coli SKF 12140 | 25 |
| Proteus vulgaris X 19 H ATCC 881 | 50 |
| Pseudomonas aeruginosa ATCC 10145 | >100 |

[a]Inoculum: $10^6$ cfu/ml
[b]Determined in the presence of 30% bovine serum

Deglucoteicoplanin was found to be very active against staphylococci (S. aureus, S. epidermidis). In particular, it was very effective against various clinical isolate methicillin-resistant staphylococci (S. aureus, S. epidermidis). Some experimental results are reported in Table II:

TABLE II

| Organism | MIC (82 g/ml) |
|---|---|
| S. aureus L 1096 | 0.05 |
| S. aureus L 1097 | 0.05 |
| S. aureus L 1524 | 0.1 |
| S. aureus L 1526 | 0.05 |
| S. epidermidis 785 | 0.05 |
| S. epidermidis 835 | 0.05 |
| S. epidermidis 1142 | 0.05 |
| S. epidermidis 1372 | 0.2 |
| S. epidermidis 1378 | 0.05 |

In experimental infection in mice infected with S. pyogenes deglucoteicoplanin exhibits an $ED_{50}$ of 0.95 mg/kg by subcutaneous administration.

Deglucoteicoplanin and its pharmaceutically acceptable salts with bases and acids can effectively be employed as the active ingredient of antimicrobial preparations used in human and veterinary medicine for the prevention and treatment of infectious diseases caused by pathogenic bacteria which are susceptible to said active ingredients.

In such treatments, these compounds may be employed as such or also in the form of mixtures in any proportion.

The compounds of the present invention can be administered orally, topically or parenterally, the parenteral administration being preferred. Depending on the route of administration, these compounds can be formulated into various dosage forms. Preparations for oral administration may be in the form of capsules, tablets, liquid solutions or suspension. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, mouth-wash or throat paints. For medication of the eyes or ears, the preparation may be presented in liquid or semi-liquid form. Topical applications may be formulated in hydrophobic or hydrophilic bases as ointments, salves, creams, lotions, paints, or powders.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution, at the time of delivery, with a suitable vehicle, such as sterile water.

The amount of active principle to be administered depends on various factors such as the size and condition of the subject to be treated, the route and frequency of administration, and the causative agent involved.

Deglucoteicoplanin and its pharmaceutically acceptable salts with bases and acids are generally effective at a daily dosage comprised between about 0.1 and about 20 mg of active ingredient per kg of body weight, preferably divided in 2 to 4 administrations per day.

Particularly desirable compositions are those prepared in the form of dosage units containing from about 5 to about 250 mg per unit.

Representative examples of preparation of pharmaceutical compositions are as follows:

A parenteral solution is prepared with
    100 mg of deglucoteicoplanin sodium salt dissolved in
    2 ml of sterile water for injection
A parenteral solution is prepared with
    250 mg of deglucoteicoplanin sodium salt dissolved in
    3 ml of sterile water for injection
A topical ointment is prepared with 200 mg of deglucoteicoplanin
3.6 g of polyethylene glycol 4000 U.S.P.
6.2 g of polyethylene glycol 400 U.S.P.

Besides their activity as medicaments, the compounds of the present invention can be used as animal growth promoters.

For this purpose, one or more of the compounds of the invention is administered orally in a suitable feed. The exact concentration employed is that which is required to provide the active agent in a growth promoting effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference.

The following examples illustrate the manner in which the invention can be practiced, but, as such, should not be construed as limiting its overall scope.

EXAMPLE 1

Preparation of deglucoteicoplanin from teicoplanin complex 10 g of teicoplanin complex, (i.e. the antibiotic complex containing teichomycin factors $A_1$, $A_2$ and $A_3$ as obtained by fermentation of strain ATCC 31121 according to U.S. Pat. No. 4,239,751), is dissolved in 90% aqueous trifluoroacetic acid (200 ml) and heated to about 80° C. for 2 hours. After cooling to room temperature, the reaction mixture is poured into ice-cooled ethyl ether (1 liter). The obtained precipitate is collected by filtration, washed with ethyl ether and then dried in the air to obtain the crude trifluoroacetic acid addition salt of deglucoteicoplanin (6.3 g).

5.3 g of this crude material is dissolved in 1 liter of a mixture of 0.2% ammonium formate/methanol/n-butanol, 1:2:3 and silanized silica gel (20 g; 0.06–0.2 mm; silanized silica gel 60; Merck) is added thereto. After appropriate stirring, the solvents are stripped off under vacuum and the residue is applied to the top of a chromatographic column prepared with 750 g of silanized silica gel (0.06–0.2 mm; Merck) in water. The column is developed with a mixture of 0.6% aqueous ammonium formate and acetonitrile, 9:1. The eluate is discarded, then the elution is continued with a linear gradient of acetonitrile/water from 1:9 to 3:7 at a rate of 200 ml/h for 30 hours.

Fractions of 25 ml each are collected and monitored by HPLC. The deglucoteicoplanin containing fractions (200 to 250) are pooled and n-butanol is added. After stirring the mixture is concentrated to a small volume, ethyl ether is added and the solid which separates is collected by filtration, washed with ethyl ether and dried at 40° C. under vacuum, yielding 0.9 g of substantially pure deglucoteicoplanin.

Crystalline deglucoteicoplanin is obtained through the following procedure:

To a suspension of 0.9 g of substantially pure deglucoteicoplanin in 250 ml of a mixture of water-/acetonitrile 90:10 (v/v) 1N HCl is added dropwise at room temperature to pH 1.7. The resulting solution is applied to a silanized silica gel column (200 g; 0.06–0.2 mm; Merck), stabilized in 1% aqueous ammonium formate, at a rate of 20 ml/hour. The column is eluted with 300 ml of distilled water which is discarded and then developed with a linear gradient of acetonitrile in water from 10% to 40% at a rate of 70 ml/hour for 30 hours. Fraction of 7 ml each are collected and monitored by HPLC. The fractions containing pure deglucoteicoplanin (221–239) are combined and allowed to stand for 24 hours at room temperature. The crystalline solid precipitate is collected by filtration, washed with a small amount (10 ml) of acetonitrile and then with ethyl ether (100 ml). This product is re-crystallized from a mixture water/acetonitrile 80:20 (v/v) and the crystalline solid thus obtained is collected by filtration, washed with ethyl ether and finally dried under vacuum (2 mmHg) for three days yielding 0.55 g of crystalline pure deglucoteicoplanin having the same physico-chemical characteristics set forth in the description above.

The hydrochloride salt of deglucoteicoplanin is prepared according to the following procedure:

A portion of 130 mg of crystalline pure deglucoteicoplanin is suspended in 10 ml of a mixture acetonitrile/water 2:3 (v/v) and 0.2 ml of 1N HCl are added thereto. After addition of 15 ml of n-butanol the resulting solution is concentrated to 2 ml under reduced pressure (20 mmHg) at 40° C. The solid precipitate which forms by addition of 10 ml of ethyl ether is collected, washed with ethyl ether on filter, and dried under vacuum at 50° C. overnight. Yield of 107 mg of deglucoteicoplanin hydrochloride.

EXAMPLE 2

Preparation of deglucoteicoplanin from antibiotic L 17046

(a) preparation of antibiotic L 17046

Antibiotic L 17046 is prepared by submitting 10 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751) to acid hydrolysis using 150 ml of 1N HCl, at 80° C., for 45 min. with stirring. Then, this mixture is cooled to 0°–5° C. and 37% hydrochloric acid (30 ml) is added. Stirring is maintained for about 10 minutes, after which the precipitated solid is recovered by filtration, washed with 20 ml of 2N HCl, then with ethyl ether, and dried overnight over potassium hydroxide pellets at room temperature, obtaining 8.3 g of crude antibiotic L 17046 hydrochloride. A portion of this product (6.2 g) is dissolved in 80% aqueous methanol (500 ml) and silica gel (30 g; 0.06–0.2 mm; Merck) is added. After the addition of n-butanol (200 ml) the solvent is removed under vacuum. The residue is then applied to a silica gel chromatography column (300 g; 0.06–0.2 mm; silica gel 60 Merck) in acetonitrile.

The column is developed using sequentially the following solvent mixtures:

| | |
|---|---|
| acetonitrile | 300 ml |
| acetonitrile/water 95:5 (v/v) | 300 ml |

| | |
|---|---|
| acetonitrile/water 90:10 (v/v) | 300 ml |
| acetonitrile/water 85:15 (v/v) | 300 ml |

The eluted fractions are discarded while the column is developed by using a linear step-gradient of acetonitrile/water from 85:15 (v/v) to about 70:30 (v/v) at a rate of 357 ml/h.

Fractions of 25 ml each are collected and monitored by HPLC. The fractions which contain antibiotic L 17046 (fractions 170 to 200) are combined. n-Butanol (400 ml) is added to the pooled fractions and the resulting mixture is concentrated to a small volume. Acetone is then added to the cloudy solution and, after cooling to about 10° C., a precipitate begins to form. After a few hours, the precipitation is complete and the solid is then collected by filtration, washed with acetone, dried under vacuum at room temperature, yielding 1.9 g of substantially pure antibiotic L 17046 having the following characteristics:

(a) the specific rotation $/\alpha/_D^{20}$ is $-44°$ (c=1%, DMF)

(b) it is freely soluble in water at pH>8.0, in dimethylformamide, dimethylsulfoxide, propyleneglycol and methylcellosolve; slightly soluble in methanol; almost insoluble in n-hexane, ethyl ether and acetone.

(c) it has an ultraviolet absorption spectrum, that exhibits the following absorption maxima:

in 0.1N hydrochloric acid: $\lambda_{max}$ 278 nm ($E_{1cm}^{1\%}=67.1$)

in 0.1N sodium hydroxide: $\lambda_{max}$ 297 nm ($E_{1cm}^{1\%}=124.1$)

in phosphate buffer pH 7.4: $\lambda_{max}$ 277 nm ($E_{1cm}^{1\%}=75.0$)

(d) an infrared absorption spectrum in nujol with the following observable absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1010, 890, 850, 820, 720 (nujol)

(e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%

(f) the following $R_f$ values in the TLC systems indicated below:

| Elution system (v/v) | $R_f$ value |
|---|---|
| (I) Acetonitrile water 75:25 (silica gel Merck 60 $F_{254}$) | 0.53 |
| (II) Acetonitrile/5% aqueous sodium sulfate 30:70 (silica gel Merck silanized 60 $F_{254}$) | 0.54 |

Visualization: UV-light at 254 nm; 3% ethanolic ninhydrine; 1% methanolic fluorescamine;

(g) a retention time ($t_R$) of 10.8 minutes when analyzed by reversed phase HPLC using a 150×4.0 mm Zorbax ® ODS (5-6 μm) column (Zorbax is a trademark of the Dupont Co. for a octadecylsilane silica matrix), and eluting with a linear gradient from 0% to 50% solution B in solution A in 40 minutes solution A: 25 mM NaH$_2$PO$_4$/acetonitrile (9/1) buffered at pH 6.0 with 0.1N NaOH solution B: 25 mM NaH$_2$PO$_4$/acetonitrile (3/7) buffered at pH 6.0 with 0.1N NaOH), with a flow rate of 2 ml/min.; (internal standard: 3,5-dihydroxytoluene $t_R$ 5.60 minutes)

(h) the $^1$H NMR spectrum registered at 270 MHz in DMSO-d$_6$ at 60° C. and with a sample concentration of 20 mg/ml (internal standard, TMS $\delta$=0.00 ppm). Some of the $^1$H NMR data obtained after D$_2$O exchange and selective decoupling experiments are as follows ($\delta$ppm, multiplicity):

1.86, s; 2.81, d; 3.5, dd; ~3–4; 4.12, d; 4.32, d; 4.37, d; 4.56, s; 4.95, ddd; 5.07, s; 5.31, d; 5.39, s; 5.51, s; 5.66, d; 6.12, d; 6.29, s; 6.32, s; 6.37, s; 6.42, s; 6.60, d; 6.62, s; 6.64, d; 6.92, d; 7.09, s; 7.12, d; 7.21, d; 7.25, d; 7.43, d; 7.64, d; 7.66, d; 7.70, d; 7.85, s; 8.12, d; 8.46, d; ~9.5, s.

(i) a potentiometric titration profile which shows three titration slopes with pH½ values equal to 5.0 (one equivalent), 7.0 (one equivalent), and 11 (five equivalents) in methylcellosolve/water 4:1 upon titration with 0.01N NaOH of the solution of the test compound containing an excess of 0.01N HCl in the same solvent mixture (l) an acidic function capable of forming salts (m) a basic function capable of forming salt (n) a sugar residue which is N-acetyl-D-glucosamine.

On the basis of the physico-chemical data and by comparison with other glycopeptidic antibiotic substances, such as vancomycin and ristocetin, the following structure can tentatively be attributed to antibiotic L 17046:

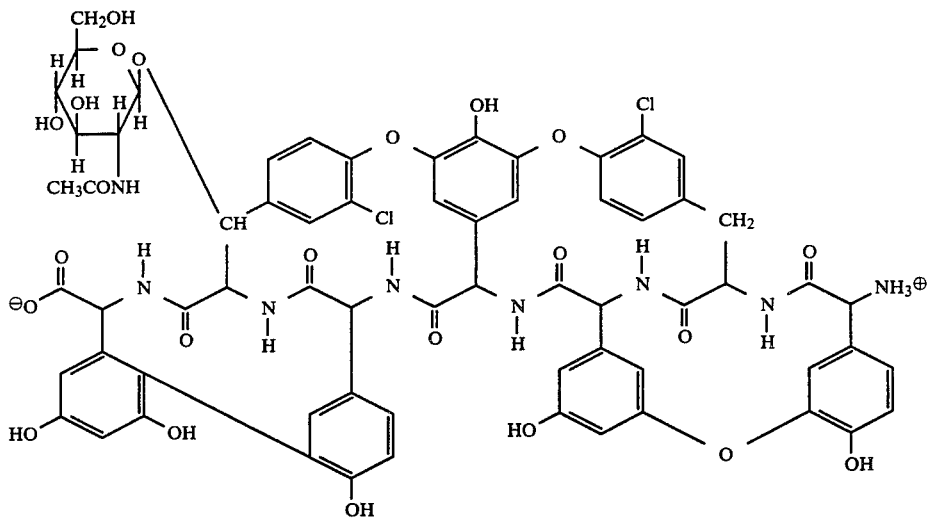

(b) preparation of deglucoteicoplanin 14 g of pure antibiotic L 17046 (prepared as above) is dissolved in 90% aqueous trifluoroacetic acid (500 ml) and heated at 80° C. for 2 hours.

After cooling to room temperature, the reaction mixture is poured into ice-cooled ethyl ether. The obtained precipitate is collected by filtration, washed with ethyl ether and dried in the air to obtain the crude trifluoroacetic acid addition salt of deglucoteicoplanin (6.3 g).

A portion of this crude material (5.3 g) are dissolved in 1 liter of a mixture of 0.2% ammonium formate/methanol/n-butanol, 1:2:3 and silanized silica gel (20 g; 0.06–0.2 mm, Merck) is added thereto. After appropriate stirring, the solvents are stripped off under vacuum and the residue is applied to the top of a chromatographic column prepared with 750 g of silanized silica gel (0.06–0.2 mm; Merck) in water. The column is developed with a mixture of 0.6% aqueous ammonium formate and acetonitrile, 9:1. The eluate is discarded, then the elution is continued with a linear gradient of an eluting mixture obtained by mixing 3 liters each of the following mixtures:

acetonitrile/water, 1:9
acetonitrile/water, 3:7
at a rate of 200 ml/h.

Fractions of 25 ml each are collected and monitored by HPLC. The deglucoteicoplanin containing fractions (200 to 250) are pooled and n-butanol is added. After stirring the mixture is concentrated to a small volume, ethyl ether is added and the solid which separates is collected by filtration, washed with ethyl ether and dried at 40° C. under vacuum, yielding 0.9 g of substantially pure deglucoteicoplanin. This product is submitted to further purification as in Example 1 yielding 0.5 g of crystalline pure deglucoteicoplanin.

EXAMPLE 3

Preparation of deglucoteicoplanin from antibiotic L 17054

(a) preparation of antibiotic L 17054

Five grams of teicoplanin complex (i.e. the antibiotic complex containing teichomycin factors $A_1$, $A_2$ and $A_3$, as obtained by fermentation of strain ATCC 31121 according to U.S. Pat. No. 4,239,751) is added to 60 ml of 0.5N aqueous hydrochloric acid pre-heated to 80° C. with vigorous stirring.

Stirring is continued and the temperature is maintained at about 80° C. for 30 minutes. Then, the mixture is rapidly filtered, the filtrate is cooled to 0°–5° C. and 6N hydrochloric acid (10 ml) is added. The resulting suspension is stirred for about 15 minutes while keeping the temperature at 0°–5° C. The precipitate is collected, washed with 20 ml of cold 1N HCl and then with ethyl ether, and dried under reduced pressure at room temperature resulting in crude antibiotic L 17054 hydrochloride (4.5 g). A sample of this product may be purified according to the following procedure:

Crude antibiotic L 17054 hydrochloride (3 g) is suspended in a mixture of 0.2% aqueous ammonium formate/acetonitrile 95:5 (v/v) (150 ml). The pH is brought to about pH 7.5 with 1 N NaOH and the product is dissolved. The resulting solution is applied to a column containing 150 g of silanized silica gel (0.06–0.2 mm, Merck) prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel (0.06–0.2 mm, Merck) in distilled water. After washing with distilled water until the salts are completely eliminated, the product is eluted with a mixture acetonitrile/water 1:1 (v/v).

The collected solution is concentrated under vacuum to a small volume and the antibiotic is precipitated by adding acetone.

After drying at room temperature, 0.9 g of pure antibiotic L 17054 is obtained. L 17054 has the following characteristics:

(a) the specific rotation $/\alpha/_D^{20}$ is $-34°(c=1\%$, DMF)

(b) it is freely soluble in water at pH>8.0, in dimethylformamide, dimethylsulfoxide, propyleneglycol and methylcellosolve; slightly soluble in methanol; almost insoluble in ethyl ether and acetone.

(c) an ultraviolet absorption spectrum which has the following absorption maxima:

in 0.1 N hydrochloric acid: $_{80}$ $_{max}$278 nm ($E_{1cm}^{1\%}=60.6$)

in 0.1 N sodium hydroxide: $\lambda_{max}$ 297 nm ($E_{1cm}^{1\%}=118.8$)

in phosphate buffer pH 7.4: $\lambda_{max}$ 277 nm ($E_{1cm}^{1\%}=70.3$)

(d) an infrared absorption spectrum in nujol with the following absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1020, 970, 890, 850, 820, 720 (nujol)

(e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67%; ashes 0.2%

(f) it has the following $R_f$ values in the TLC systems indicated below:

| Elution system (v/v) | $R_f$ value |
|---|---|
| (I) Acetonitrile/water 75:25 (silica gel Merck 60 F$_{254}$) | 0.32 |
| (II) Acetonitrile/5% aqueous sodium sulfate 30:70 (silica gel Merck silanized 60 F$_{254}$) | 0.61 |

Visualization: UV-light at 254 nm; 3% ethanolic ninhydrine; 1% methanolic fluorescamine;

(g) a retention time ($t_R$) of 8.3 minutes when analyzed by HPLC using a 150×4.0 mm Zorbax ® ODS (5-6 μm) column (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$/acetonitrile 9:1, buffered at pH 6.0 with 0.1 N NaOH; solution B: 25 mM NaH$_2$PO$_4$/acetonitrile 3:7, buffered at pH 6.0 with 0.1 N NaOH), with a flow rate of 2 ml/min.; (internal standard: 3,5-dihydroxytoluene $t_R$ 5.60 minutes)

(h) the $^1$H NMR spectrum is registered at 270 MHz in DMSO-d$_6$ at 60° C. and with a sample concentration of 20 mg/ml (internal standard TMS, δ=0.00 ppm). Some of the $^1$H NMR data obtained after D$_2$O exchange and selective decoupling experiments are as follows (δppm, multiplicity): 1.88, s; 2.85, d; ~3.5, dd; 3-4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d.

(i) a potentiometric titration profile which shows three titration slopes with pH$\frac{1}{2}$ values equal to 5.0 (one equivalent), 7.0 (one equivalent), and 11 (five equivalents) in methylcellosolve/water 4:1 upon titrating a solution of the test compound containing an excess of 0.01 N HCl in methylcellosolve/water 4:1 with 0.01 N NaOH in the same solvent mixture (l) an acidic function capable of forming salts (m) a basic function capable of forming salts (n) two sugar residues which are D-mannose and N-acetyl-D-glucosamine.

On the basis of the physico-chemical data and by comparison with the structures known for other glycopeptidic antibiotic substances, such as vancomycin and ristocetin, the following structure can tentatively be attributed to antibiotic L 17054:

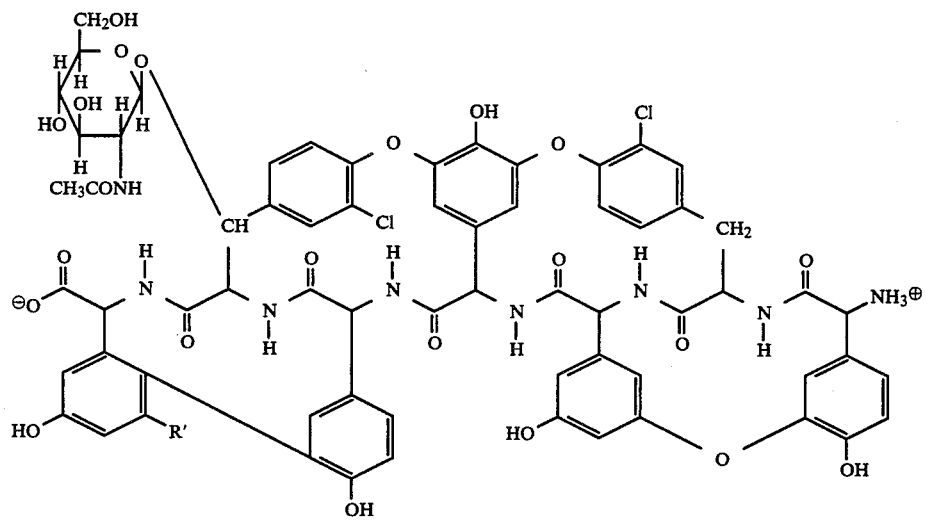

wherein R' represents the group formula

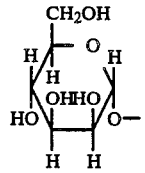

(b) preparation of deglucoteicoplanin

A solution of 2.0 g of crude antibiotic L 17054 in 50 ml of 90% aqueous trifluoroacetic acid is heated at 80° C for 2 hours. After cooling to room temperature, the reaction mixture is poured into ice-cooled ethyl ether (400 ml). The obtained precipitate is filtered off, washed with ethyl ether and dried in the air obtaining crude deglucoteicoplanin as the trifluoroacetic acid addition salt, (1.12 g) which is then purified as described in Example 1, yielding 0.7 g of crystalline pure deglucoteicoplanin.

EXAMPLE 4

Preparation of deglucoteicoplanin from teicoplanin complex

Ten grams of teicoplanin complex (i.e. the antibiotic complex containing teichomycin factors $A_1$, $A_2$ and $A_3$, as obtained by fermentation of strain ATCC 31121 according to U.S. Pat. No. 4,239,751) are suspended in 80 ml of benzyl alcohol and 20 ml of 37% (w/v) aqueous HCl is added to the mixture at about 40° C. The mixture is stirred under vacuum (20 mmHg) for 12 hours at 60° C. while adding every one and an half hour a mixture of 5 ml of 37% aqueous HCl and 15 ml of benzyl alcohol.

At the end of the reaction, the mixture is cooled to room temperature and one liter of ethyl ether is added thereto. The crude precipitate is collected, washed with acetone and with ethyl ether, and then it is dried under vacuum at 40° C. overnight yielding 9.2 g of a crude product. Said crude product is dissolved in 250 ml of a mixture of methanol and 0.1 N HCl 3:2 (v/v) and to the resulting solution one liter of a mixture of water/ethyl acetate/n-butanol 4:5:1 (v/v/v) is added. The pH of the aqueous phase is adjusted to 8.5 by addition of 1 N NaOH and the organic layer is then discarded. The aqueous phase is applied at the top of a chromatographic column prepared with 750 g of silanized silica gel (0.06-0.2 mm; Merck) in water. The column is developed with a mixture of 0.6% aqueous ammonium formate and acetonitrile 9:1. The eluate is discarded, then the elution is continued with a linear gradient of an eluting mixture obtained by mixing 3 liters each of the following mixtures:

acetonitrile/water, 1:9
acetonitrile/water, 3:7
at a rate of 200 ml/hour.

Fractions of 25 ml each are collected and monitored by HPLC. The deglucoteicoplanin containing fractions (200 to 250) are pooled and n-butanol is added. After stirring the mixture is concentrated to a small volume, ethyl ether is added and the solid which separates is collected by filtration, washed with ethyl ether and dried at 40° C. under vacuum, yielding 1.5 g of substantially pure deglucoteicoplanin.

EXAMPLE 5

Preparation of deglucoteicoplanin from teicoplanin factor $A_2$

Five grams of teicoplanin factor $A_2$ (i.e. teichomycin $A_2$ as obtained according to U.S. Pat. No. 4,239,751) are treated in the same manner as described in the Example 4. The yield of substantially pure deglucoteicoplanin is 0.85 g.

EXAMPLE 6

Preparation of deglucoteicoplanin from teicoplanin complex

To a suspension of 5 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751) in 80 ml of 1-octanol, are added 20 ml of 37% (w/v) aqueous HCl at about 40° C. and the mixture is heated at 65° C. and stirred under vacuum for 13 hours. During the reaction time, additions of a mixture of 5 ml of 37% aqueous HCl and 15 ml of 1-octanol are repeated every two hours. At the end of the reaction, the mixture is cooled to room temperature and then poured into 800 ml of ethyl ether. The solid which precipitates is washed with acetone and dried under vacuum at 40° C. overnight. The crude product thus obtained is then worked up according to the last part of Example 4, yielding 0.6 g of substantially pure deglucoteicoplanin.

Example 7

Preparation of deglucoteicoplanin from a mixture of teicoplanin factors $A_2$ and $A_3$ Five grams of a mixture of teicoplanin factors $A_2$ and $A_3$ (80% by weight factor $A_2$, 10% by weight factor $A_3$, the remaining part being water and mineral salts) is suspended in 80 ml of 1-octanol and 20 ml of 2 N $H_2SO_4$ are added dropwise while cooling. The reaction mixture is then transferred into a rotary evaporator and then heated at 65° C. for 1 hour, at atmospheric pressure and for further 30 minutes under vacuum (20 mmHg) to remove most of the water. After stirring at 65° C. for additional 20 hours the reaction mixture is cooled to room temperature and then poured into 800 ml of ethyl ether. The precipitate is collected on filter and then dissolved in 1 liter of a mixture methanol/water 1:3 (v/v). The resulting solution is extracted twice with 500 ml of ethyl acetate and the organic layers are discarded. The aqueous layer is then extracted twice with 500 ml of n-butanol and the alcoholic solution is concentrated to a small volume. By addition of 500 ml of acetone a solid precipitate is obtained which is collected on filter and dried under vacuum at 40° C. for 18 hours, yielding 2.25 g of a crude product which is then worked up as in the second part of Example 1 yielding 0.75 g of crystalline pure deglucoteicoplanin.

Example 8

Preparation of deglucoteicoplanin from antibiotic L 17046

Antibiotic L 17046 (5.4 g) is suspended in 90 ml of n-octanol and 25 ml of 2 N $H_2SO_4$ is added dropwise while cooling at $-5°$ C. The reaction is then carried out in a rotary evaporator as described in Example 7. Stirring is continued for 18 hours and the product is isolated and purified as described in the same Example 7 yielding 0.3 g of crystalline pure deglucoteicoplanin.

Example 9

Preparation of deglucoteicoplanin from teicoplanin factor $A_2$

A suspension of 5 g of teicoplanin factor $A_2$ (i.e. teichomycin $A_2$ as obtained according to U.S. Pat. No. 4,239,751) in 150 ml of 1-pentanol saturated with 37% (w/v) aqueous HCl is stirred at 70° C. for 6 hours. Then most water is gradually removed under reduced pressure (20 mmHg) and the cloudy solution is stirred at room temperature for additional 2 hours. Ethyl ether (300 ml) is then added to the reaction mixture and the solid precipitated is collected by filtration, washed with ethyl ether and dried under vacuum at 40° C. for 18 hours over potassium hydroxide yielding 4.6 g of a crude yellow powder. This crude product is dissolved in 500 ml of a mixture of n-butanol/methanol/water 7:1:2 (v/v/v). The resulting solution is extracted twice with 250 ml of water while adjusting the pH of the aqueous layer to 9 by addition of 0.1 N NaOH. The combined aqueous layers are concentrated to small volume under reduced pressure (20 mmHg). Then 0.1 N HCl is added to pH 5.6 and the solid which separates is collected by filtration, washed with ethyl ether and dried at 40° C. for three days giving 0.88 g of a crude product which is worked up as in the last part of Example 4. Yield 0.51 g of substantially pure deglucoteicoplanin.

EXAMPLE 10

Preparation of deglucoteicoplanin from teicoplanin complex 2.5 g of teicoplanin complex (i.e. the antibiotic containing teichomycin factors $A_1$, $A_2$ and $A_3$, as obtained by fermentation of strain ATCC 31121 according to U.S. Pat. No. 4,239,751) are treated in the same manner as described in Example 9 above by employing the appropriate proportions of solvents and reagents. The yield of substantially pure teicoplanin is 0.16 g.

EXAMPLE 11

Preparation of deglucoteicoplanin from teicoplanin complex 20 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751; the water content determined by Karl-Fischer method is 12% by weight) is suspended in 300 ml of 0.5 N hydrogen chloride solution in absolute trifluoroethanol and the suspension is heated at 80° C. under stirring while continuously bubbling anhydrous hydrogen chloride for 12 hours. After cooling to room temperature, the reaction mixture is filtered and the solid collected is washed with ethyl ether and then suspended in water (1 liter). The pH of the water suspension is adjusted to 1.9 by addition of 1 N HCl and the solution obtained is washed with 1 liter of ethyl acetate (discarded), and then extracted with 1 liter of a mixture n-butanol/ethyl acetate 1:2 (v/v). The organic phase is washed with water saturated with NaCl (500 ml) and then concentrated to small volume. By addition of 500 ml of ethyl ether a solid precipitate forms which is collected by filtration, washed with ethyl ether and dried in the air yielding 18.6 g of crude product. This crude product is dissolved in 1 liter of methanol and 25 g of silanized silica gel (0.06–0.2 mm; Merck) is added and the solvent is stripped off in vacuo at 35° C. The residue is suspended in 500 ml of a mixture of acetonitrile/5% aqueous ammonium formate 1:9 and applied at the top of a column prepared with 2.5 kg of the same silanized silica gel, buffered with 1 liter of 10% aqueous ammonium formate and stabilized with 500 ml of a mixture of acetonitrile/5% ammonium formate 1:9. The column is then washed with 2 liters of a mixture of water/acetonitrile 1:9 and then developed with 8 liters of a linear gradient from 10% to 40% (v/v) of acetonitrile in water. Fractions of 20 ml each are collected and examined by HPLC. Fraction 71 to 420 are combined, and after addition of n-butanol (4 liters) are concentrated to a small volume. By addition of ethyl ether, a precipitate is obtained which is collected by filtration, washed with ethyl ether and then dried in the air yielding 6.5 g of substantially pure deglucoteicoplanin. Crystalline pure deglucoteicoplanin is obtained by submitting this product to the same procedure as described in the last part of Example 1. Yield 3.5 g of crystalline pure deglucoteicoplanin having the physico-chemical characteristics described in the specification above.

EXAMPLE 12

Preparation of deglucoteicoplanin from a mixture of teicoplanin factors $A_2$ and $A_3$ Ten grams of a mixture of teicoplanin factors $A_2$ and $A_3$ (80% by weight:factor $A_2$; 9.5 by weight:factor $A_3$; 10,0% by weight:water; 0,5% by weight:inorganic salts) are submitted to the same procedure of Example 11 by using the appropriate proportions of reagents and solvents. Yield 4 g of substantially pure deglucoteicoplanin. From two grams of this product, 1.15 g of crystalline pure deglucoteicoplanin are obtained.

EXAMPLE 13

Preparation of deglucoteicoplanin from teicoplanin factor $A_2$, component 2.

1.5 g of teicoplanin factor $A_2$, component 2 (obtained according to British Patent Application No. 2,121,401 where it is identified as Teichomycin $A_2$, factor 2) containing 10% of water (Karl-Fischer method), is submitted to the same procedure of the first part of Example 11 by employing the appropriate proportions of solvents and reagents. Yield 1.2 g of crude product. This crude product is directly submitted to the purification procedure for obtaining crystalline pure deglucoteicoplanin described in the last part of Example 1. Yield 450 mg of crystalline pure deglucoteicoplanin.

EXAMPLE 14

Preparation of deglucoteicoplanin from teicoplanin complex 2.5 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751, the water content determined by Karl-Fischer method is 13.5% by weight) is suspended in 50 ml of trichloroethanol and the mixture is stirred at 90° C. for 12 hours while continuously bubbling anhydrous hydrogen chloride. The reaction mixture is then worked up as in Example 11 yielding 700 mg of substantially pure deglucoteicoplanin.

EXAMPLE 15

Preparation of deglucoteicoplanin from antibiotic L 17046

Antibiotic L 17046 (1.5 g) is suspended in 35 ml of trichloroethanol and then treated as in Example 13. Yield 475 mg of substantially pure deglucoteicoplanin.

EXAMPLE 16

Preparation of deglucoteicoplanin from teicoplanin complex 2.65 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751), is dissolved with stirring into 180 ml of acetic acid. To this solution 20 ml of 37% (w/v) HCl are added and the mixture is heated at 80° C. for one hour (the reaction time has been determined according to previous experiments where the reaction was followed by HPLC). After cooling to room temperature, the reaction mixture is poured into 1 liter of ice-cooled ethyl ether. The obtained precipitate is collected by filtration, washed with ethyl ether and then dissolved in 60 ml of a mixture of methanol and 0.1 N HCl 3:2 (v/v). To the resulting solution, 600 ml of a mixture of water/ethyl acetate/n-butanol 4:5:1 (v/v/v) are added and the pH is adjusted to 8.5 by adding 1 N NaOH. The organic layer is then discarded and the aqueous phase chromatographed through a column prepared with 270 g of silanized silica gel as described in the last part of Example 4. Yield 750 g of substantially pure deglucoteicoplanin.

EXAMPLE 17

Preparation of deglucoteicoplanin from Teicoplanin factor $A_2$ 2.55 g of teicoplanin factor $A_2$ (i.e. teichomycin $A_2$ as obtained according to U.S. Pat. No. 4,239,751) is suspended with stirring in 160 ml of acetic acid and then 16 ml of 40% (w:v) HBr is added to the reaction mixture. After heating at 80° C. for one hour the mixture is cooled to room temperature and poured into 1 liter of ethyl ether. The crude precipitate is washed with ethyl ether and then worked up as in Example 16 yielding 16 mg of substantially pure deglucoteicoplanin.

EXAMPLE 18

Preparation of deglucoteicoplanin from teicoplanin complex 2.5 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751), is dissolved into 150 ml of acetic at 80° C. To this solution, 480 mg of DO-WEX ® HCR-S (a strong acid cation exchanger styrene-divinyl benzene sulfonated resin in the hydrogen form; standard mesh size: 20–50. The resin is previously anhydrified by washing with five portions, each of 100 ml of methanol and then dried in the air overnight) and 0.13 ml of water are added. The mixture is vigorously stirred for 20 hours and then the resin is filtered off and washed twice with 100 ml portions of acetic acid containing 10% (v/v) of 37% (w/v) aqueous HCl. The organic solution are combined and poured into 2 liters of ethyl ether. The crude precipitate is washed with ethyl ether and then worked up as in Example 4 yielding 600 mg of substantially pure deglucoteicoplanin.

EXAMPLE 19

Preparation of deglucoteicoplanin from antibiotic L 17046

Antibiotic L 17046 (2.5 g) is dissolved in 150 ml of acetic acid at 80° C. This solution is treated in the same manner as in Example 18. The crude product (precipitated by addition of ethyl ether) is purified as in the last part of Example 4 yielding 900 mg of substantially pure deglucoteicoplanin.

EXAMPLE 20

Deglucoteicoplanin from teicoplanin complex 10 g of teicoplanin complex (i.e. the antibiotic complex containing teichomycin factors $A_1$, $A_2$ and $A_3$, as obtained by fermentation of strain ATCC 31121 according to U.S. Pat. No. 4,239,751; the water content determined by Karl-Fischer method is 10.5% by weight) is suspended in 100 ml of 0.5 N hydrogen chloride solution in 1,1,1,3,3,3-hexafluoro-2-propanol and the suspension is heated at 70° C. with stirring while continuously bubbling anhydrous hydrogen chloride for 20 hours. Then the reaction mixture is worked up as in Example 11 yielding 3.8 g of substantially pure deglucoteicoplanin. From 0.8 g of this sample are obtained 0.5 g of crystalline pure deglucoteicoplanin by employing the procedure described in the last part of Example 1.

EXAMPLE 21

Deglucoteicoplanin from teicoplanin factor $A_2$.

1.5 g of teicoplanin factor $A_2$, component 2 (obtained according to British Patent Application No. 2,121,401 where it is identified as teichomycin $A_2$, factor 2) containing 10% of water (Karl-Fischer method), is submitted to the same procedure of the first part of Example 20 by employing the appropriate proportions and reagents. Yield 550 mg of substantially pure deglucoteicoplanin.

We claim:

1. A process for transforming a teicoplanin compound or a teicoplanin-like compound into deglucoteicoplanin and its salts with bases and acids characterized in that a substance selected from teicoplanin complex, any further purified preparation thereof, teicoplanin factor $A_2$, teicoplanin factor $A_3$, each of the main components of teicoplanin factor $A_2$, a teicoplanin-like compound of the formula

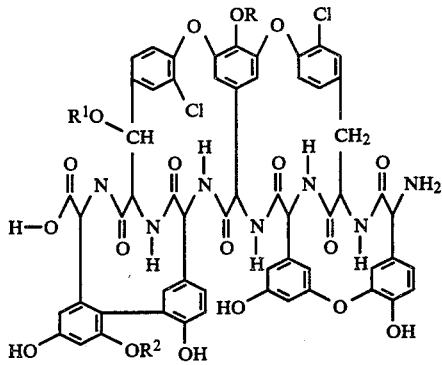

wherein
R is hydrogen,
$R^1$ is hydrogen or a N-acetyl-D-glucosamine group,
$R^2$ is hydrogen or a D-mannose group with the proviso that R, $R^1$, and $R^2$ cannot be simultaneously hydrogen, and a mixture of two or more of any of the above substances in any proportion is submitted to controlled strong acid hydrolysis
wherein the controlled strong acid hydrolysis conditions are provided by employing (a) an organic protic solvent selected from aliphatic acids and alphahalogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry ($C_1$-$C_4$) alkyl, ($C_1$-$C_4$) alkoxy or halo groups which ar the reaction temeprature are liquids slightly mixable with water, and betapolyhalogenated lower alkanols, which at the reaction temperature are liquids, (b) a strong acid compatible with the solvent selected from strong mineral acids, strong organic acids and strong acid cation exchanger resins in the hydrogen form, and (c) a reaction temperature between about 20° C. and about 100° C.

2. A process as in claim 1 wherein the organic protic solvent is selected from aliphatic acids and alpha halogenated aliphatic acids.

3. A process as in claim 2 wherein the organic protic solvent is selected from aliphatic acids of 1 to 5 carbon acid and the strong acid is selected from concentrated aqueous mineral acids and strong acid cation exchanger resins in the hydrogen form.

4. A process as in claim 2 wherein the organic protic solvent is acetic acid, the strong acid is selected from hydrochloric acid, hydrobromic acid, sulfuric acid and the strong acid cation exchanger resins in the hydrogen form, and the reaction temperature is between 65° C. and 85° C.

5. A process as in claim 2 wherein the organic protic solvent is selected from alpha-halogenated aliphatic acids of 2 to 5 carbon atoms and is acting also as strong acid promoting the hydrolysis reaction.

6. A process as in claim 5 wherein the alpha-halogenated aliphatic acid is aqueous trifluoroacetic acid at a concentration between 75% and 90% and the reaction temperature is between 60° and 90° C.

7. A process as in claim 6 wherein the concentration of the acid is about 90% and the reaction temperature is about 80° C.

8. A process of claim 1 wherein the organic protic solvent is selected from aliphatic alkanols and cycloaliphatic alkanols of at least five carbon atoms which at the reaction temperature are liquid slightly mixable with water.

9. A process as in claim 8 wherein the organic protic solvent is selected from primary and secondary alkanols and secondary cycloalkanols of 5 to 10 carbon atoms, the strong acid is a concentrated aqueous mineral acid and the reaction temperature is between 35° C. and 100° C.

10. A process as in claim 9 wherein the organic protic solvent is 1-octanol, the concentrated aqueous mineral acid is selected from concentrated aqueous hydrochloric acid, concentrated aqueous hydrobromic acid and concen-trated aqueous sulfuric acid and the reaction temperature is between 40° C. and 80° C.

11. A process as in claim 1 wherein the organic protic solvent is selected from phenyl substituted lower alkanols wherein the phenyl moiety may optionally carry ($C_1$-$C_4$)alkyl, ($C_1$-$C_4$)alkoxy or halo rests which at the reaction temperature are slightly mixable with water.

12. A process as in claim 11 wherein the organic solvent is selected from phenyl substituted lower alkanols wherein the lower alkanol portion is a primary or secondary alcohol portion of 1 to 4 carbon atoms and the strong acid is a concentrated aqueous mineral acid and the reaction temperature is between 35° C. and 100° C.

13. A process as in claim 12 wherein the organic protic solvent is benzyl alcohol, the concentrated aqueous mineral acid is selected from concentrated hydrochloric acid, concentrated hydrobromic acid and concentrated sulfuric acid and the reaction temperature is between 40° C. and 80° C.

14. A process as in claim 1 wherein the organic protic solvent is selected from beta-polyhalogenated lower alkanols of 1 to 4 carbon atoms.

15. A process as in claim 14 wherein the strong acid is a hydrogen halide selected from hydrogen chloride and hydrogen bromide and the reaction temperature is between 40° C. and 80° C.

16. A process as in claim 15 wherein the organic protic solvent is selected from trifluoroethanol and 1,1,1,3,3,3-hexafluoro-2-propanol and the hydrogen halide is selected from hydrogen chloride and hydrogen bromide.

17. A process as in claim 1 wherein the organic protic solvent consist of a mixture of two or more solvents.

18. A process as in claim 1 wherein the deglucoteicoplanin planin is obtained in the form of a salt thereof with a base or an acid.

19. A process as in any of the claims 1 to 19 wherein the controlled strong acid hydrolysis reaction is carried out in the presence of water.

* * * * *

UNITED STATES PATENT AND TRADEMARK OFFICE
CERTIFICATE OF CORRECTION

PATENT NO. : 4,629,781

DATED : December 16, 1986

INVENTOR(S) : Paolo Strazzolini et al.

It is certified that error appears in the above-identified patent and that said Letters Patent is hereby corrected as shown below:

At column 1, line 49, and again at column 28, line 33, in the structure, the patent reads:

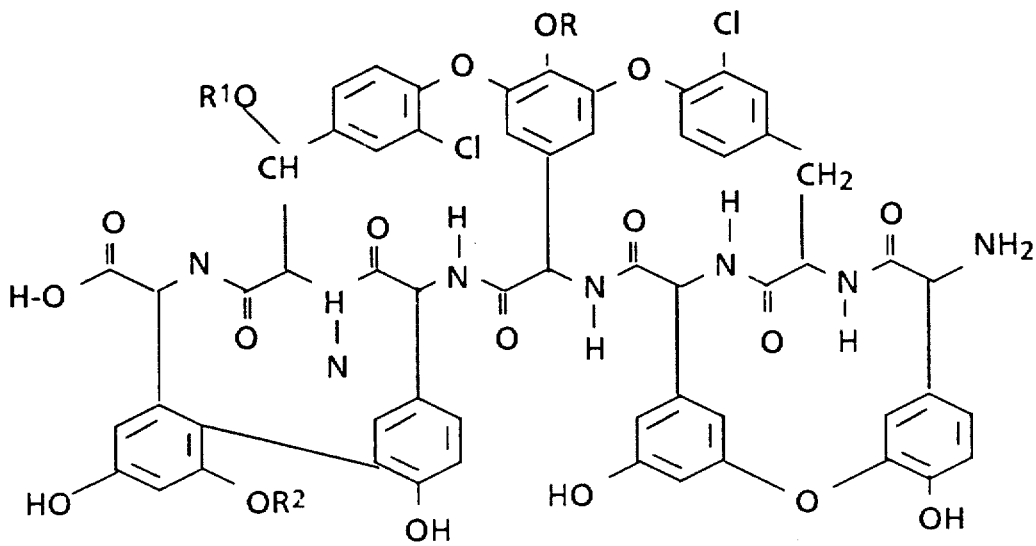

and should read:

UNITED STATES PATENT AND TRADEMARK OFFICE
CERTIFICATE OF CORRECTION

PATENT NO. : 4,629,781

DATED : December 16, 1986

INVENTOR(S) : Paolo Strazzolini et al.

It is certified that error appears in the above-identified patent and that said Letters Patent is hereby corrected as shown below:

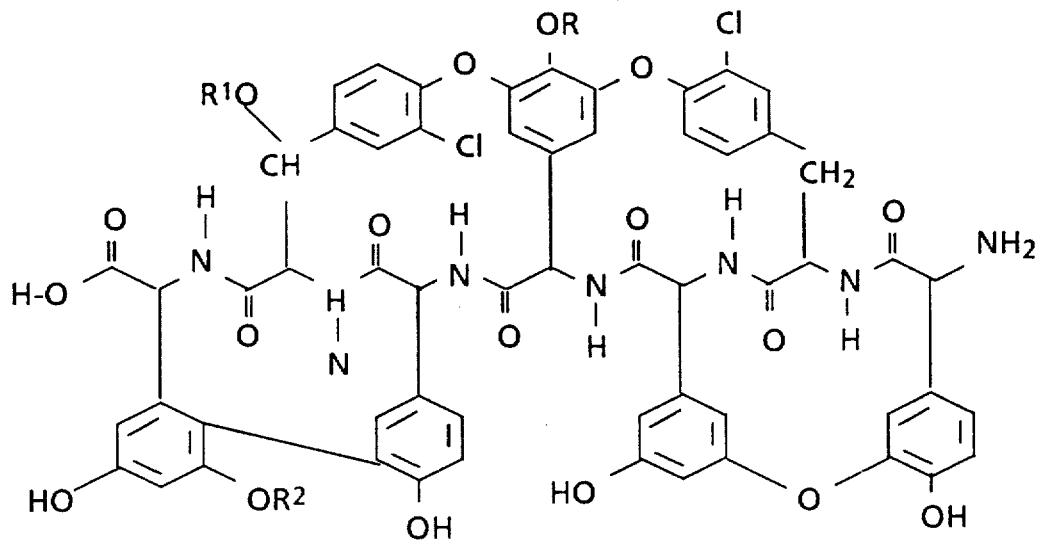

At column 5, line 3, the patent reads "1-hexanol2-hexanol" and should read --1-hexanol, 2-hexanol--.
At column 5, line 12, the patent reads "cyclooctanol2,3" and should read --cyclooctanol, 2,3--.
At column 6, line 59, the patent reads "are compatible each other" and should read --are compatible with each other--.
At column 11, line 9, the patent reads "wavelenght)" and should read --wavelength)--.
At column 13, line 59, the patent reads "MIC (82g/ml)" and should read --MIC (µg/ml)--

UNITED STATES PATENT AND TRADEMARK OFFICE
CERTIFICATE OF CORRECTION

PATENT NO. : 4,629,781

DATED : December 16, 1986

INVENTOR(S) : Paolo Strazzolini et al.

It is certified that error appears in the above-identified patent and that said Letters Patent is hereby corrected as shown below:

At column 20, line 67, the patent reads "80 max 278 nm" and should read --$\lambda_{max}$ 278 nm--.
At column 24, line 19, the patent reads "for additional 20 hours" and should read --for an additional 20 hours--.
At column 24, line 61, the patent reads "disselved" and should read --dissolved--.
At column 28, line 58, the patent reads "ar the reaction temeprature" and should read --at the reaction temperature--.
At column 29, line 38, the patent reads "concen-trated" and should read --concentrated--.
At column 30, lines 33-34, the patent reads "deglucoteico-planin planin is" and should read --deglucoteicoplanin is--.

Signed and Sealed this

Eleventh Day of July, 1989

Attest:

DONALD J. QUIGG

Attesting Officer

Commissioner of Patents and Trademarks